United States Patent [19]

King

[11] Patent Number: 4,797,387

[45] Date of Patent: Jan. 10, 1989

[54] CERTAIN PHARMACEUTICALLY USEFUL UREAS

[75] Inventor: Francis D. King, Harlow, England

[73] Assignee: Beecham Group, p.l.c., Middlesex, England

[21] Appl. No.: 3,222

[22] Filed: Jan. 14, 1987

[30] Foreign Application Priority Data

Jan. 16, 1986 [GB] United Kingdom ............... 8600978
Oct. 31, 1986 [GB] United Kingdom ............... 8626042

[51] Int. Cl.$^4$ ................... A61K 31/46; C07D 451/04
[52] U.S. Cl. ................................. 514/212; 514/214; 514/216; 514/299; 514/304; 514/305; 514/323; 514/339; 514/412; 514/413; 540/582; 540/597; 540/602; 546/112; 546/124; 546/125; 546/133; 546/200; 546/272; 548/452
[58] Field of Search .............. 546/112, 124, 125, 133, 546/452, 200, 272; 540/582, 597, 602; 514/212, 214, 216, 299, 304, 305, 323, 339, 412, 413; 548/452

[56] References Cited

U.S. PATENT DOCUMENTS 4,432,983 2/1984 Riley et al. ...................... 546/125

FOREIGN PATENT DOCUMENTS 0158265 10/1985 European Pat. Off. .
2100259 12/1982 United Kingdom .
2125398 3/1984 United Kingdom .

Primary Examiner—Mary C. Lee
Assistant Examiner—Bernard I. Dentz
Attorney, Agent, or Firm—James F. Haley, Jr.; David K. Barr

[57] ABSTRACT

Compounds of formula (I), and pharmaceutically acceptable salts thereof:

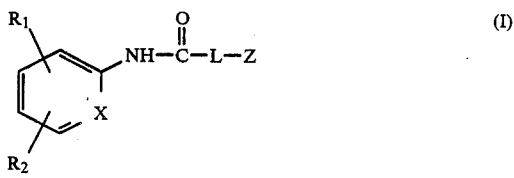

wherein
L is NH or O;
X is a moiety capable of hydrogen bonding to the NH group depicted in formula (I);
$R_1$ and $R_2$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, carboxy, $C_{1-6}$ alkoxycarbonyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene; and
Z is a group of formula (a), (b) or (c)

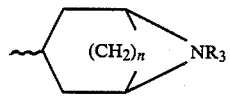

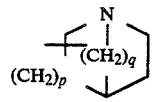

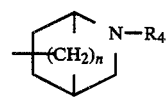

wherein n is 2 or 3; p is 1 or 2; q is 1 to 3; r is 1 to 3; and
$R_3$ or $R_4$ is $C_{1-7}$ alkyl, $C_{3-8}$ cycloalkyl, $C_{3-8}$ cycloalkyl-$C_{1-2}$ alkyl or $C_{2-7}$ alkylenyl-$C_{1-4}$ alkyl; having 5-HT M-receptor antagonist activity, a process for their preparation and their use as pharmaceuticals.

12 Claims, No Drawings

CERTAIN PHARMACEUTICALLY USEFUL UREAS

This invention relates to novel compounds having useful pharmacological properties, to pharmaceutical compositions containing them, to processes and intermediates for their preparation, and to their use as pharmaceuticals.

GB Nos. 2100259A and 2125398A and EP-A-No. 158265 describe benzoates and benzamides having an azabicyclic side chain and possessing 5-HT antagonist activity.

A class of novel, structurally distinct compounds has now been discovered. These compounds have 5-HT M-receptor antagonist activity, anti-emetic activity and/or gastric motility enhancing activity.

Accordingly, the present invention provides a compound of formula (I), or a pharmaceutically acceptable salt thereof:

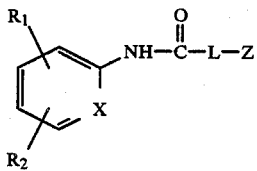

wherein
L is NH or O;
X is a moiety capable of hydrogen bonding to the NH group depicted in formula (I);
$R_1$ and $R_2$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, carboxy, $C_{1-6}$ alkoxycarbonyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl, $C_{1-4}$ alkyl, phenyl or phenyl $C_{1-4}$ alkyl groups or optionally N-disubstituted by $C_{4-5}$ polymethylene; and
Z is a group of formula (a), (b) or (c)

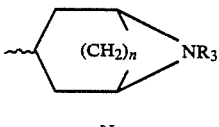

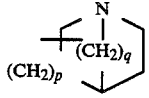

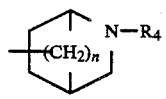

wherein n is 2 or 3; p is 1 or 2; q is 1 to 3; r is 1 to 3; and
$R_3$ or $R_4$ is $C_{1-7}$ alkyl, $C_{3-8}$ cycloalkyl, $C_{3-8}$ cycloalkyl-$C_{1-2}$ alkyl or $C_{2-7}$ alkenyl-$C_{1-4}$ alkyl.
Preferably L is NH.
X is usually C—$OR_5$ wherein $R_5$ is hydrogen, $C_{1-6}$ alkyl, $C_{3-7}$ alkenyl-methyl, phenyl or phenyl $C_{1-4}$ alkyl in which either phenyl moiety may be substituted by one or two $C_{1-6}$ alkyl, $C_{1-6}$ alkoxy or halo (such as fluoro, chloro or bromo) or X is a moiety C—$R_6$ wherein $R_6$ is $CO_2R_7$ wherein $R_7$ is hydrogen or $C_{1-6}$ alkyl, $CONR_8R_9$ or $SO_2NR_8R_9$ wherein $R_8$ and $R_9$ are independently hydrogen or $C_{1-6}$ alkyl or together are $C_{4-6}$ polymethylene, $NO_2$, $(CH_2)_mOR_{10}$ wherein m is 1 or 2 and $R_{10}$ is $C_{1-6}$ alkyl or $S(O)_nR_{11}$ wherein n is 0, 1 or 2 and $R_{11}$ is $C_{1-6}$ alkyl. X may also be $N^+$—$O^-$.

Suitable examples of alkyl groups in $R_5$, $R_7$, $R_8$, $R_9$, $R_{10}$ and $R_{11}$ include methyl, ethyl, n- and iso-propyl, n-, sec-, iso- and tert-butyl, preferably methyl.

Suitable values for $R_5$ when $C_{3-7}$ alkenyl-methyl include prop-2-enyl, but-2-enyl, but-3-enyl, 1-methylenepropyl and 1-methylprop-2-yl in their E and Z forms where stereoisomerism exists.

Preferred examples of X include C—$OCH_3$, C—$OC_2H_5$, C—$OC_3H_7$, C—$CO_2CH_3$, C—$CO_2C_2H_5$ and $SO_2N(CH_3)_2$.

Values for $R_1$ and/or $R_2$ include hydrogen, fluoro, chloro, bromo, $CF_3$, methyl, ethyl, methoxy, ethoxy, methylthio, ethylthio, acetyl, propionyl, acetylamino, methylsulphonylamino, methylsulphinyl, carboxy, methoxycarbonyl, hydroxy, nitro; and amino, aminocarbonyl, aminosulphonylamino or N-(aminosulphonyl)-methylamino any of which may be optionally substituted by one or two methyl groups or by a cyclopentyl or cyclohexyl group or disubstituted by $C_4$ or $C_5$ polymethylene; $R_1$ is often hydrogen and $R_2$ is hydrogen or a 4-substituent, such as halo or methoxy. $R_1$ and $R_2$ are preferably both hydrogen.

Preferably n is 2 or 3 and p, q and r are 1 or 2.

Examples of $R_3/R_4$ when $C_{1-7}$ alkyl include as groups of interest $C_{1-3}$ alkyl such as methyl, ethyl and n- and iso-propyl. Within $C_{1-7}$ alkyl, $C_{4-7}$ alkyl are also of interest, especially those of the formula $(CH_2)_uR_9$ wherein u is 1 or 2 and $R_9$ is a secondary or tertiary $C_{3-6}$ alkyl group. Examples of $C_{4-7}$ alkyl include n-, sec- and tert-butyl, n-pentyl, n-heptyl, and iso-butyl, 3-methylbutyl, and tert-butylmethyl.

Examples of $R_3/R_4$ when $C_{3-8}$ cycloalkyl-$C_{1-2}$ alkyl include in particular those wherein the cycloalkyl moiety is cyclohexyl or cyclopropyl. Examples of include cyclopropylmethyl, cyclobutylmethyl, cyclopentylmethyl, cyclohexylmethyl, cyclopropylethyl, cyclobutylethyl, cyclopentylethyl, cyclohexylethyl, tert-butylmethyl, iso-propylmethyl, iso-propylethyl and tert-butylethyl.

$R_3/R_4$ may in particular be cyclopropylmethyl, cyclohexylmethyl, iso-propylmethyl, tert-butylmethyl or iso-propylethyl, preferably tert-butylmethyl.

Examples of $R_3/R_4$ when $C_{2-7}$ alkenyl-$C_{1-4}$ alkyl include prop-2-enyl, but-2-enyl, but-3-enyl and 1-methylprop-2-enyl in their E and Z forms when stereoisomerism exists.

$R_3/R_4$ is preferably methyl or ethyl, most preferably methyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, lactic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_{10}$-T wherein $R_{10}$ is $C_{1-6}$ alkyl, phenyl-$C_{1-6}$ alkyl or $C_{5-7}$ cycloalkyl, and T is a radical corresponding to an anion of an acid. Suitable examples of $R_{10}$ include methyl, ethyl and n- and iso-propyl; and benzyl and phenethyl. Suitable examples of T include halides such as chloride, bromide and iodide.

The compounds of formula (I) may also form internal salts such as pharmaceutically acceptable N-oxides.

The compounds of the formula (I), and their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of formula (I) may adopt an endo or exo configuration with respect to L. The endo configuration is preferred.

A group of compounds within formula (I) is of formula (II):

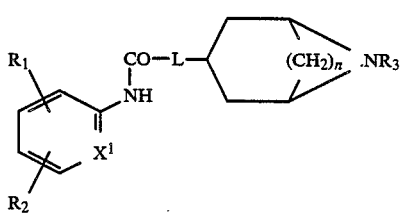

(II)

wherein $X^1$ is $COR_5$ or a group $C-R_6$ as hereinbefore defined; and the remaining variables are as defined in formula (I).

Examples of the variables and preferred variables are as so described for corresponding variables in relation to formula (I).

A further group of compounds within formula (I) is of formula (III):

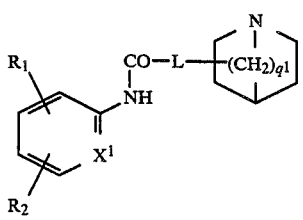

(III)

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

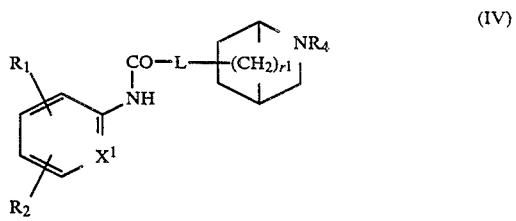

(IV)

wherein $r^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

(V)

with a compound of formula (VI):

$$J-Z^1$$

(VI)

wherein E is:

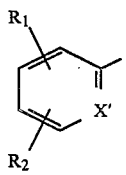

wherein X' is X as defined, or N, and Y is hydrogen or joined to G as defined, or (when X is $N^+-O^-$) E and Y together are joined to G to form (V)'

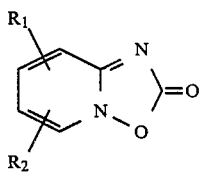

G is $COQ_1$ where $Q_1$ is a group displaceable by a nucleophile, G and Y together are $=C=O$ or G is joined to E as defined, or G is hydrogen (when Y is hydrogen); and, when G is $COQ_1$ or G—N—Y is $N=C=O$, J is $NH_2$, or OH or a reactive derivative thereof or, when G is hydrogen, J is a group containing an activated carbonyl group capable of forming a CO—L-linkage with the compound of formula (V); $Z^1$ is Z as defined or Z wherein $R_3/R_4$ is replaced by a hydrogenolysable protecting group; and the remaining variables are as hereinbefore defined; and thereafter optionally converting any $R_1$ and $R_2$ group to another $R_1$ and $R_2$ group respectively, converting $Z^1$, when other than Z, to Z; converting X' when N to $N^+$—$O^-$ or X to other X; and optionally forming a pharmaceutically acceptable salt of the resultant compound of formula (I).

Examples of leaving groups $Q_1$, displaceable by a nucleophile, include halogen such as chloro and bromo, $C_{1-4}$ alkoxy, such as $CH_3O$ and $C_2H_5O$—, PhO— or activated hydrocarbyloxy, such as $Cl_5C_6O$— or $Cl_3CO$—.

If a group $Q_1$ is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group $Q_1$ is $C_{1-4}$ alkoxy, phenoxy or activated hydrocarbyloxy then the reaction is preferably carried out in an inert polar solvent, such as toluene or dimethylformamide. It is also preferred that the group $Q_1$ is $Cl_3CO$— and that the reaction is carried out in toluene at reflux temperature.

In a preferred process variant, G and Y together are $=C=O$ in which case the reaction takes place in an inert solvent, such as ether, at 0°–100° C., preferably ambient temperature.

When L is OH or a reactive derivative thereof, the reactive derivative is often a salt, such as the lithium, sodium or potassium salt.

When the compound of formula (V) is (V)', the reaction takes place under similar conditions as described above for $Q_1$ is halide.

When G is hydrogen, J—$Z^1$ may be a compound of formula (VII) or (VIII) when L is NH; or of formula (IX) when L is O:

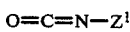  (VII)

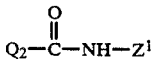  (VIII)

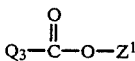  (IX)

wherein
$Z^1$ is as hereinbefore defined, and $Q_2$ and $Q_3$ are leaving groups, preferably $Cl_3CO$.

When J—$Z^1$ is of formula (VII), the reaction is preferably carried out in an inert solvent, under conventional conditions, at 0°–100° C.

$Q_2$ is a leaving group as defined for $Q_1$ hereinafter; and the reaction is carried out in accordance with the conditions described herein for the reaction wherein G is $COQ_1$.

Examples of $Q_3$, displaceable by a nucleophile, include halogen, such as chloro and bromo; and activated hydrocarbyloxy, such as $Cl_5C_6O$— and $Cl_3CO$.

If a group $Q_3$ is a halide, the reaction is carried out as described above for $Q_1$ halide.

If $Q_3$ is activated hydrocarbyloxy, the reaction is carried out as described for $Q_1$ activated hydrocarbyloxy.

The invention provides a further process for the preparation of a compound of formula (I), or a pharmaceutically acceptable salt thereof, which process comprises reacting a compound of formula (X):

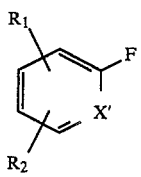  (X)

with a compound of formula (XI):

  (XI)

wherein M is a metal ion and the remaining variables are as hereinbefore defined; and thereafter optionally converting $Z^1$, when other than Z, to Z; converting X' when N is $N^+$—$O^-$ or X to other X; and optionally forming a pharmaceutically acceptable salt of the resultant compound of formula (I).

Examples of M include alkali metals such as sodium and potassium.

The reaction may be carried out at ambient temperature or below in an inert solvent such as tetrahydrofuran or dimethylsulphoxide.

It will be apparent that compounds of the formula (I) containing an $R_1$ or $R_2$ group which is convertible to another $R_1$ or $R_2$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a $C_{1-7}$ acylamino substituent is convertible to an amino substituent by deacylation;

(iv) an amino substituent is convertible to a $C_{1-4}$ acylamino substituent by acylation with a carboxylic acid derivative;

(v) a hydrogen substituent is convertible to a halogen substituent by halogenation;

(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;

(vii) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene, by N-alkylation;

(viii) an amino substituent is convertible to a $C_{1-6}$ alkylsulphonylamino group or an aminosulphonylamino group optionally N-substituted as defined by acylation with a $C_{1-6}$ alkylsulphonyl chloride or di-substituted aminosulphonyl chloride;

(ix) A $C_{1-4}$ alkylamino substituent group is convertible to a N-($C_{1-6}$ alkylsulphonyl)N-$C_{1-4}$ alkylamino group or an N-(amino sulphonyl)N-$C_{1-4}$ alkylamino group optionally N-substituted as defined by acylation with a $C_{1-6}$ alkylsulphonyl chloride or di-substituted aminosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N-moiety of a side chain (a), (b) or (c) and suitable precautions will routinely be taken by those skilled in the art.

In regard to (vii), alkylation is carried out with a corresponding alkylating agent such as the chloride or bromide under conventional conditions.

$Z^1$ when other than Z may have a hydrogenolysable protecting group which is benzyl optionally substituted by one or two groups as defined for $R_1$ and $R_2$. Such benzyl groups may, for example, be removed, when $R_1$ or $R_2$ is not halogen, by conventional transition metal catalysed hydrogenolysis to give compounds of the formula (XII):

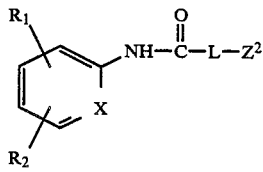
(XII)

wherein $Z^2$ is of formula (d) or (e)

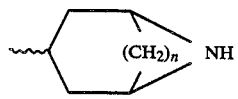
(d)

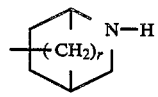
(e)

wherein the variables are as defined in formula (I).

This invention also provides a further process for the preparation of a compound of the formula (I) which comprises N-alkylating a compound of formula (XII), and optionally forming a pharmaceutically acceptable salt, of the resulting compound of the formula (I).

In this further process of the invention 'N-alkylation' comprises the substitution of the N-atom depicted in formula (XII) by any group $R_3/R_4$ as hereinbefore defined. This may be achieved by reaction of the compound of formula (XII) with a compound $R_3Q_4$ or $R_4Q_4$ wherein $R_3$ and $R_4$ are as hereinbefore defined and $Q_4$ is a leaving group.

Suitable values for $Q_4$ include groups displaced by nucleophiles such as Cl, Br, I, $OSO_2CH_3$ or $OSO_2C_6H_4pCH_3$.

Favoured values for $Q_4$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slightly above.

Alternatively, 'N-alkylation' may be effected under conventional reductive alkylation conditions when the group $R_3$ or $R_4$ in the compound of formula (I) contains a methylene group adjacent to the N-atom in the bicycle.

Interconverting $R_3$ or $R_4$ in the compound of the formula (XII) before coupling with the compound of the formula (V) is also possible. Such interconversions are effected conveniently under the above conditions. It is desirable to protect any amine function with a group readily removable by acidolysis such as $C_{2-7}$ alkanoyl group, before $R_3/R_4$ interconversion.

When $R_3$ or $R_4$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_3$ or $R_4$ is methyl, where the methyl group is replaced by esterified carboxyl. Such compounds may then be reduced using a strong reductant such as lithium aluminium hydride to the corresponding compound of formula (VI).

Compounds of formula (I) wherein X' is N may be converted to compounds of formula (I) wherein X is $N^+$—$O^-$ by conventional oxidation, using, for example, hydrogen peroxide or m-chloroperbenzoic acid.

Compounds of formula (I) wherein $R_6$ is $CO_2H$ may be converted to compounds of formula (I) wherein $R_6$ is $CO_2R_7^1$ wherein $R_7^1$ is $C_{1-6}$ alkyl, or $R_6$ is $CONR_8R_9$ by conventional esterification or animation respectively.

The compounds of formula (V) and (VI) are known or are preparable analogously to, or routinely from, known compounds.

Compounds of the formula (VI) wherein Z is of formula (c) may be prepared as described in European Patent Publication No. 115933 or by analogous methods thereto.

Compounds of the formula (XII) are novel and form an aspect of the invention.

It will be realised that in the compound of the formula (I) the —CO—L—linkage may have an endo or exo orientation with respect to the ring of the bicyclic moiety to which it is attached. A mixture of endo and exo isomers of the compound of the formula (I) may be synthesized non-stereospecifically and the desired isomer separated conventionally therefrom e.g. by chromatography; or alternatively the endo and exo isomer may if desired be synthesised from the corresponding endo or exo form of the compound of the formula (VI).

Pharmaceutically acceptable salts of the compounds of this invention may be formed conventionally. The acid addition salts may be formed, for example, by reaction of the base compound of formula (I) with a pharmaceutically acceptable organic or inorganic acid.

The compounds of the present invention are 5-HT antagonists and it is thus believed may generally be used in the treatment of prophylaxis of migraine, cluster headaches and trigeminal neuralgia. Compounds which are 5-HT antagonists may also be of potential use in the treatment of CNS disorders such as anxiety and psychosis; arrhythmia, obesity and irritable bowel syndrome.

The compounds of the present invention also have anti-emetic activity; in particular that of preventing cytotoxic agent or radiation induced nausea and vomiting. Examples of cytotoxic agents include cisplatin, doxorubicin and cyclophosphamide.

The compounds of the present invention also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for constitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.1 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I).

N.B. Nomenclature is based on Chemical Abstracts Index Guide 1977 published by the American Chemical Society.

EXAMPLE 1

(endo)-N-(9-Methyl-9-azabicyclo[3.3.1]non-3-yl)-N'-2-methoxyphenyl urea (E1)

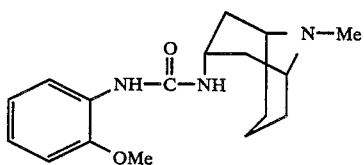

To a stirred solution of (endo)-9-methyl-9-azabicyclo[3.3.1]-nonan-3-amine (1.6 g) in Et$_2$O (50 ml) at 0° C. was added dropwise a solution of 2-methoxyphenyl isocyanate (1.5 g) in Et$_2$O (5 ml). The reaction mixture was then stirred at room temperature overnight and the title compound (E1) collected by filtration and dried (2.5 g 80%).
m.p. 203°–4° C.
Prepared similarly was:

EXAMPLE 2

(endo)-N-(8-methyl-8-azabicyclo[3.2.1]oct-3-yl)-N'-2-methoxyphenyl urea (E2)

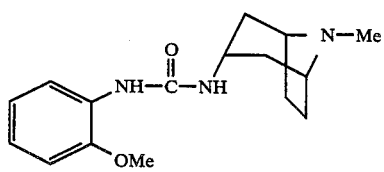

m.p. 210°–11°.

| $^1$H—NMR (CDCl$_3$, 79.5 MHz) | |
|---|---|
| δ | 8.00–7.75 (m, 1H) |
| | 7.20–6.70 (m, 4H) |
| | 5.25 (d, 1H) |
| | 4.20–3.75 (m, 4H including 3.85, s, 3H) |
| | 3.20–2.95 (m, 2H) |
| | 2.50–1.50 (m, 11H) |

EXAMPLE 3

(endo)-N-(8-Methyl-8-azabicyclo[3.2.1]oct-3-yl)-N'-(2-pyridyl-1-oxide)urea (E3)

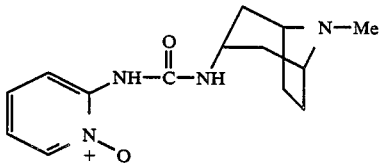

A solution of (endo)-8-methyl-8-azabicyclo[3,2,1]octan-3-amine (0.7 g) and pyridino[1',2'-2,3]-1-oxa-2,4-diazol-5-one (0.65 g) in xylene (25 ml) was heated under reflux under N$_2$ for 18 h. The reaction mixture was allowed to cool, concentrated in vacuo and the residue purified by column chromatography on alumina to give the title compound (0.6 g) m.p. 229°–31° (dec).

| $^1$H NMR (CDCl$_3$, 270 MHz) | |
|---|---|
| δ | 10.04 (s, 1H) |
| | 8.48 (dm, 1H) |
| | 8.11 (dm, 1H) |
| | 7.48 (brd, 1H) |
| | 7.37 (tm, 1H) |
| | 6.87 (tm, 1H) |
| | 4.00 (q, 1H) |
| | 3.13 (brs, 2H) |
| | 2.35–2.20 (m, 5H including 2.28, s, 3H) |
| | 2.05–1.75 (m, 6H) |

EXAMPLE 4 TO 27

The following examples were prepared by a procedure analogous to that used for Example 1.

(endo)-O-(8-Methyl-8-azabicyclo[3.2.1]oct-3-yl)-N'-(2-methoxyphenyl)carbamate monohydrochloride (E4)

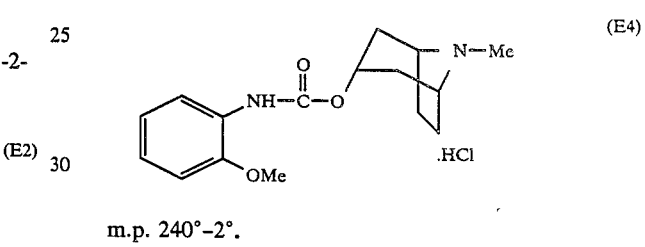

m.p. 240°–2°.

| $^1$H NMR (CDCl$_3$, 270 MHz) | |
|---|---|
| δ | 8.00 (brd, 1H) |
| | 7.15–6.85 (m, 4H) |
| | 5.14 (t, 1H) |
| | 3.88 (s, 3H) |
| | 3.78 (brd, 2H) |
| | 3.20–2.00 (m, 11H including 2.78, s, 3H) |

(endo)-N-(8-Methyl-8-azabicyclo[3.2.1]oct-3-yl)-N'-(5-fluoro-2-methoxyphenyl)urea (E5)

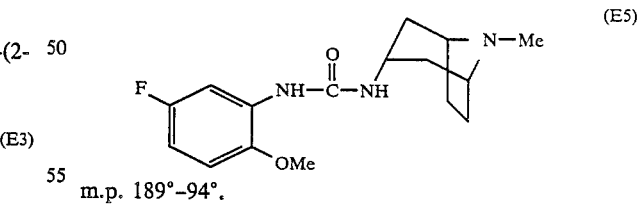

m.p. 189°–94°.

| $^1$H NMR (CDCl$_3$ + CD$_3$OD) | |
|---|---|
| δ | 7.95 (dd, 1H) |
| | 6.77 (dd, 1H) |
| | 6.58 (dt, 1H) |
| | 3.99–3.80 (m, 4H including 3.86, s, 3H) |
| | 3.20 (brs. 2H) |
| | 2.33 (s, 3H) |
| | 2.30–1.95 (m, 8H) |
| | 1.77 (brd, 2H) |

(endo)-N-(8-Methyl-8-azabicyclo[3.2.1]oct-3-yl)-N'-(2,4-dimethoxyphenyl)urea (E6)

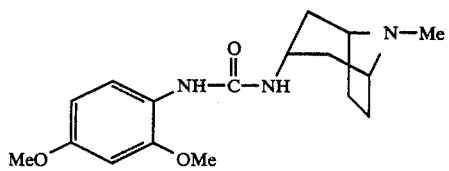

m.p. 170°–1°.

| $^1$H NMR (CDCl$_3$ 400 MHz) | |
|---|---|
| δ | 7.58 (d, 1H) |
| | 6.40–4.40 (m, 3H including 6.49, s, 1H) |
| | 5.24 (brd, 1H) |
| | 3.96 (q, 1H) |
| | 3.80 (s, 6H) |
| | 3.12 (brs, 2H) |
| | 2.27 (s, 3H) |
| | 2.25–2.15 (m, 2H) |
| | 2.08–1.98 (m, 2H) |
| | 1.72–1.62 (m, 3H) |

(endo)-N-(8-Methyl-8-azabicyclo[3.2.1]oct-3-yl)-N'-(2-methoxy-5-methylphenyl)urea (E7)

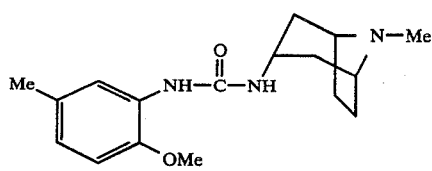

m.p. 190°–1°.

| $^1$H NMR (CDCl$_3$, 270 MHz) | |
|---|---|
| δ | 7.73 (brs, 1H) |
| | 6.85–6.70 (m, 3H) |
| | 5.31 (brd, 1H) |
| | 3.98 (q, 1H) |
| | 3.80 (s, 3H) |
| | 3.13 (brs, 2H) |
| | 2.35–2.00 (m, 10H including 2.29, s, 3H and 2.26 s, 3H) |
| | 1.85–1.64 (m, 4H) |

(endo)-N-(8-Methyl-8-azabicyclo[3.2.1]oct-3-yl)-N'-(5-chloro-2-methoxyphenyl)urea monohydrochloride (E8)

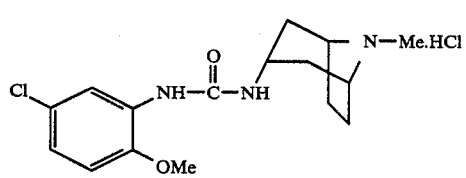

m.p. 259°–63°.

| $^1$H NMR (d$^6$-DMSO, 400 MHz) | |
|---|---|
| δ | 10.90 (brs, 1H) |
| | 8.30–8.20 (m, 2H) |

| $^1$H NMR (d$^6$-DMSO, 400 MHz) | |
|---|---|
| | 7.28 (d, 1H) |
| | 6.85–6.80 (m, 2H) |
| | 3.96 (q, 1H) |
| | 3.89 (s, 3H) |
| | 3.85–3.70 (m, 2H) |
| | 2.80–2.65 (m, 5H) |
| | 2.55–2.45 (m, 2H) |
| | 2.30–2.20 (m, 2H) |
| | 2.09 (brd, 2H) |

(endo)-N-(8-Methyl-8-azabicyclo[3.2.1]oct-3-yl)-N'-(2,5-dimethoxyphenyl)urea (E9)

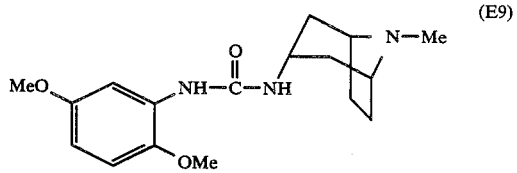

m.p. 192°.

| $^1$H NMR (CDCl$_3$, 270 MHz) | |
|---|---|
| δ | 7.72 (d, 1H) |
| | 6.98 (brd, 1H) |
| | 6.78 (d, 1H) |
| | 6.51 (dd, 1H) |
| | 5.36 (brm, 1H) |
| | 4.00 (q, 1H) |
| | 3.80 (s, 3H) |
| | 3.76 (s, 3H) |
| | 3.16 (brs, 2H) |
| | 2.35–2.20 (m, 5H including 2.30, s, 3H) |
| | 2.15–2.05 (m, 2H) |
| | 1.98–1.67 (m, 4H) |

(endo)-N-(8-Methyl-8-azabicyclo[3.2.1]oct-3-yl)-N'-(2-methoxy-5-nitrophenyl)urea monohydrochloride (E10)

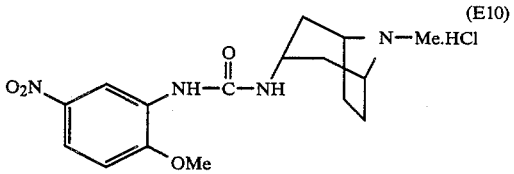

m.p. 237°–250°.

| $^1$H NMR (CDCl$_3$/d$^6$-DMSO; 400 MHz) | |
|---|---|
| δ | 10.40 (brs, 1H) |
| | 9.12 (d, 1H) |
| | 8.51 (s, 1H) |
| | 7.83 (dd, 1H) |
| | 7.41 (d, 1H) |
| | 7.07 (d, 1H) |
| | 4.04 (s, 3H) |
| | 3.94 (q, 1H) |
| | 3.85 (brs, 2H) |
| | 2.72 (d, 3H) |
| | 2.66–2.52 (m, 2H) |
| | 2.48–2.16 (m, 4H) |
| | 2.08 (d, 2H) |

(endo)-N-(8-Methyl-8-azabicyclo[3.2.1]oct-3-yl)-N'-(2-methoxy-4-methoxycarbonylphenyl)urea (E11)

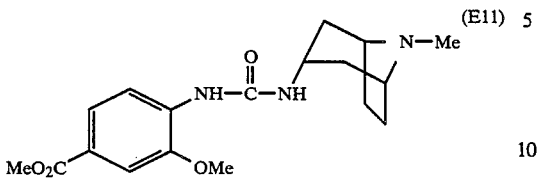

m.p. 108°–112°.

| $^1$H NMR (CDCl$_3$, 400 Hz) | |
|---|---|
| δ | 8.24 (d, 1H) |
| | 7.64 (dd, 1H) |
| | 7.50–7.44 (m, 2H) |
| | 5.76 (brd, 1H) |
| | 4.02 (q, 1H) |
| | 3.90 (s, 3H) |
| | 3.83 (s, 3H) |
| | 3.15 (brs, 2H) |
| | 2.34–2.20 (m, 5H including 2.30, s, 3H) |
| | 2.14–2.00 (m, 2H) |
| | 1.92–1.80 (m, 2H) |
| | 1.72 (d, 2H) |

(endo)-N-(8-Methyl-8-azabicyclo[3.2.1]oct-3-yl)-N'-(2-ethoxy-5-fluorophenyl)urea (E12)

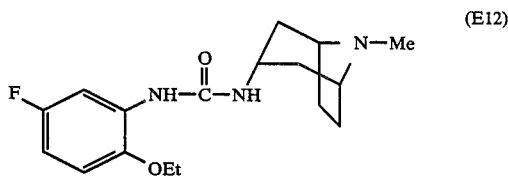

m.p. 185°–8°.

| $^1$H NMR (CD$_3$OD, 79.5 MHz) | |
|---|---|
| δ | 7.92 (dd, 1H) |
| | 6.92 (dd, 1H) |
| | 6.61 (dt, 1H) |
| | 4.30–3.75 (m, 3H) |
| | 3.20 (brs, 2H) |
| | 2.50–1.25 (m, 14H including 2.34, s, 3H and 1.46, t, 3H) |

(endo)-N-(8-Methyl-8-azabicyclo[3.2.1]oct-3-yl)-N'-(4-fluoro-2-methoxyphenyl)urea (E13)

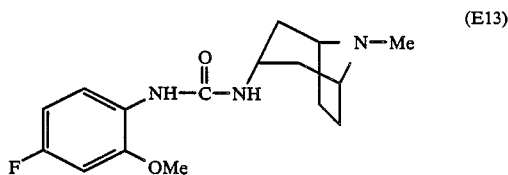

m.p. 191°–4°.

| $^1$H NMR (CD$_3$OD 270 MHz) | |
|---|---|
| δ | 7.89 (dd, 1H) |
| | 6.75 (dd, 1H) |
| | 6.57 (dt, 1H) |

| $^1$H NMR (CD$_3$OD 270 MHz) | |
|---|---|
| | 4.00–3.80 (m, 4H including 3.87, s, 3H) |
| | 3.22–3.05 (m, 2H) |
| | 2.32–1.65 (m, 13H including 2.27, s, 3H) |

N-(1-Azabicyclo[2.2.2]oct-3-yl)-N'-(2-methoxyphenyl)urea (E14)

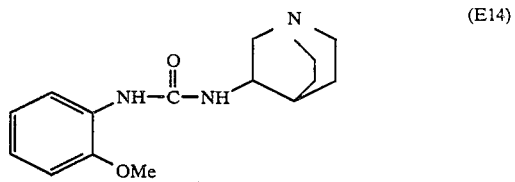

m.p. 197°–8°.

| $^1$H NMR (CDCl$_3$, 270 MHz) | |
|---|---|
| | 8.15–8.00 (m, 1H) |
| | 7.06–6.80 (m, 4H) |
| | 5.28 (brd, 1H) |
| | 3.96–3.80 (m, 4H including 3.83, s, 3H) |
| | 3.36 (m, 1H) |
| | 2.95–2.70 (m, 4H) |
| | 2.53 (dd, 1H) |
| | 1.98 (brs, 1H) |
| | 1.80–1.60 (m, 3H) |
| | 1.55–1.40 (m, 1H) |

O-(1-Azabicyclo[2.2.2]oct-3-yl)-N'-(2-methoxyphenyl)carbamate monohydrochloride (E15)

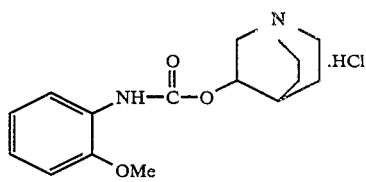

m.p. 227°–9°.

| $^1$H NMR (d$^6$-DMSO, 270 MHz) | |
|---|---|
| δ | 10.50 (brs, 1H) |
| | 8.62 (s, 1H) |
| | 7.67 (d, 1H) |
| | 7.12–7.00 (m, 2H) |
| | 6.98–6.86 (m, 1H) |
| | 5.00–4.90 (m, 1H) |
| | 3.82 (s, 1H) |
| | 3.65 (dd, 1H) |
| | 3.40–3.00 (m, 7H) |
| | 2.28 (brs, 1H) |
| | 2.15–1.65 (m, 4H) |

(endo)-N-(8-Methyl-8-azabicyclo[3.2.1]oct-3-yl)-N'-(2-n-propyloxyphenyl)urea (E16)

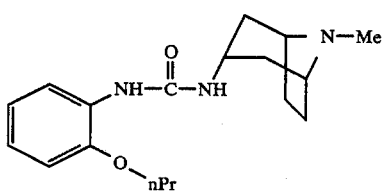

m.p. 163°–5°.

| $^1$H NMR (CDCl$_3$, 270 MHz) | |
|---|---|
| δ | 7.85 (dd, 1H) |
| | 7.05–6.84 (m, 3H) |
| | 6.77 (brs, 1H) |
| | 5.23 (brd, 1H) |
| | 4.00–3.88 (m, 3H including 3.97, t, 2H) |
| | 3.17 (brs, 2H) |
| | 2.35–2.20 (m, 5H including 2.30, s, 3H) |
| | 2.12–2.02 (m, 2H) |
| | 1.90–1.66 (m, 6H) |
| | 1.02 (t, 3H) |

(endo)-N-(8-Methyl-8-azabicyclo[3.2.1]oct-3-yl)-N'-(2-ethoxyphenyl)urea (E17)

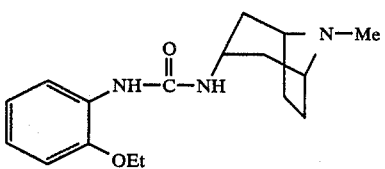

m.p. 170°–5°.

| $^1$H NMR (CDCl$_3$, 400 MHz) | |
|---|---|
| δ | 7.90 (dd, 1H) |
| | 7.04–6.82 (m, 4H) |
| | 5.52 (brd, 1H) |
| | 4.07 (q, 2H) |
| | 3.95 (q, 1H) |
| | 3.15 (brs, 2H) |
| | 2.35–2.20 (m, 5H including 2.30, s, 3H) |
| | 2.10–2.00 (m, 2H) |
| | 1.85–1.68 (m, 4H) |
| | 1.42 (t, 3H) |

(endo)-N-(8-Methyl-8-azabicyclo[3.2.1]oct-3-yl)-N'-(5-dimethylaminocarbonyl-2-methoxyphenyl)urea (E18)

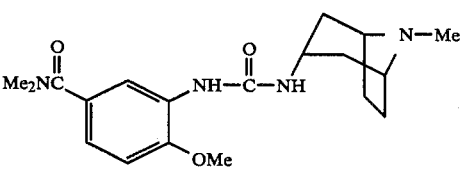

| $^1$H NMR (CDCl$_3$, 270 MHz) | |
|---|---|
| δ | 8.09 (d, 1H) |
| | 7.21 (brs, 1H) |

-continued

| $^1$H NMR (CDCl$_3$, 270 MHz) | |
|---|---|
| | 7.03 (dd, 1H) |
| | 6.87 (d, 1H) |
| | 5.84 (brd, 1H) |
| | 3.93 (q, 1H) |
| | 3.80 (s, 3H) |
| | 3.15 (brs, 2H) |
| | 3.06 (s, 6H) |
| | 2.32 (s, 3H) |
| | 2.32–2.16 (m, 2H) |
| | 2.15–1.87 (m, 4H) |
| | 1.71 (brd, 2H) |

(endo)-N-(8-Methyl-8-azabicyclo[3.2.1]oct-3-yl)-N'-(5-methoxycarbonyl-2-methoxyphenyl)urea (E19)

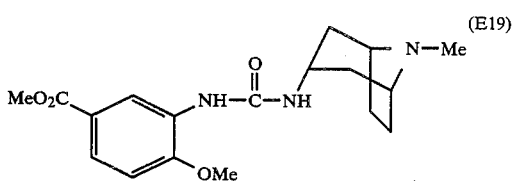

m.p. 125°–6°.

| $^1$H NMR (CDCl$_3$, 270 MHz) | |
|---|---|
| δ | 8.64 (d, 1H) |
| | 7.73 (dd, 1H) |
| | 7.01 (brs, 1H) |
| | 6.86 (d, 1H) |
| | 5.53 (brd, 1H) |
| | 4.00 (q, 1H) |
| | 3.97 (s, 3H) |
| | 3.95 (s, 3H) |
| | 3.18 (brs, 2H) |
| | 2.35–2.20 (m, 5H including 2.31, s, 3H) |
| | 2.18–2.05 (m, 2H) |
| | 1.92–1.79 (m, 4H) |

(endo)-N-(8-Methyl-8-azabicyclo[3.2.1]oct-3-yl)-N'-(2-iso-propoxyphenyl)urea (E20)

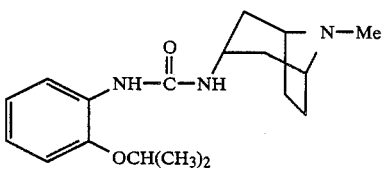

m.p. 163°–4°.

| $^1$H—NMR (CDCl$_3$, 270 MHz) | |
|---|---|
| δ | 7.87 (dd, 1H) |
| | 7.01–6.86 (m, 3H) |
| | 6.78 (brs, 1H) |
| | 5.20 (brd, 1H) |
| | 4.56 (m, 1H) |
| | 3.94 (m, 1H) |
| | 3.17 (brs, 2H) |
| | 2.30 (s, 3H) |
| | 2.27–2.20 (m, 2H) |
| | 2.10–2.03 (m, 2H) |
| | 1.80–1.68 (m, 4H) |
| | 1.35 (d, 6H) |

(endo)-N-(8-Methyl-8-azabicyclo[3.2.1]oct-3-yl)-N'-(2-benzyloxyphenyl)urea (E21)

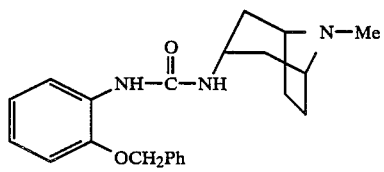

(E21)

m.p. 174°–6°.

| $^1$H—NMR(CDCl$_3$, 270 MHz) | |
|---|---|
| δ | 7.91 (dd, 1H) |
| | 7.43–7.32 (m, 5H) |
| | 7.00–6.90 (m, 3H) |
| | 7.78 (brs, 1H) |
| | 5.13 (brd, 1H) |
| | 5.06 (s, 2H) |
| | 3.88 (m, 1H) |
| | 3.11 (brs, 2H) |
| | 2.27 (s, 3H) |
| | 2.23–2.12 (m, 2H) |
| | 2.08–2.12 (m, 2H) |
| | 1.78–1.60 (m, 4H) |

(endo)-N-(8-Methyl-8-azabicyclo[3.2.1]oct-3-yl)-N'-(2-hydroxyphenyl)urea hydrochloride (E22)

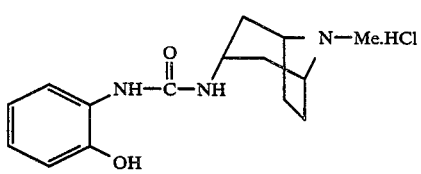

(E22)

m.p. 267°–8°.

| $^1$H—NMR (d$^6$-DMSO, 270 MHz) | |
|---|---|
| δ | 10.33 (brs, 1H) |
| | 9.96 (s, 1H) |
| | 8.28 (s, 1H) |
| | 7.88 (dd, 1H) |
| | 7.18 (d, 1H) |
| | 6.84–6.63 (m, 3H) |
| | 3.80 (brm, 3H) |
| | 2.65 (s, 3H) |
| | 2.50–2.37 (m, 2H) |
| | 2.30–2.15 (m, 4H) |
| | 1.96–1.82 (m, 2H) |

(endo)-N-(8-Methyl-8-azabicyclo[3.2.1]oct-3-yl)-N'-(2-sec-butyloxyphenyl)urea (E23)

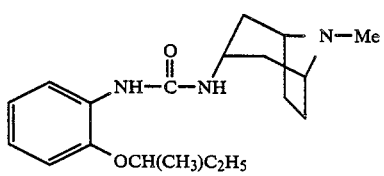

(E23)

m.p. 136°–7°.

| $^1$H—NMR (CDCl$_3$, 270 MHz) | |
|---|---|
| δ | 7.87 (dd, 1H) |
| | 7.00–6.78 (m, 4H) |
| | 5.20 (brd, 1H) |
| | 4.33 (m, 1H) |
| | 3.93 (m, 1H) |
| | 3.14 (brs, 2H) |
| | 2.31–2.17 (m, 5H including 2.28, s, 3H) |
| | 2.10–2.01 (m, 2H) |
| | 1.80–1.57 (m, 6H) |
| | 1.28 (d, 3H) |
| | 0.98 (t, 3H) |

(endo)-N-(8-Methyl-8-azabicyclo[3.2.1]oct-3-yl)-N'-(2-n-butyloxyphenyl)urea (E24)

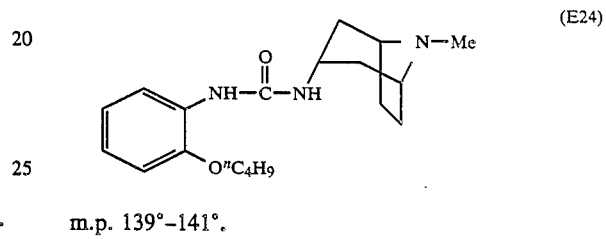

(E24)

m.p. 139°–141°.

| $^1$H—NMR (CDCl$_3$, 270 MHz) | |
|---|---|
| δ | 7.86 (dd, 1H) |
| | 7.02–6.83 (m, 3H) |
| | 6.76 (s, 1H) |
| | 5.19 (brd, 1H) |
| | 4.00 (t, 2H) |
| | 3.93 (m, 1H) |
| | 3.15 (brs, 2H) |
| | 2.28 (s, 3H) |
| | 2.25–2.17 (m, 2H) |
| | 2.11–2.03 (m, 2H) |
| | 1.81–1.65 (m, 6H) |
| | 1.47 (m, 2H) |
| | 0.98 (t, 3H) |

(endo)-N-(8-Methyl-8-azabicyclo[3.2.1]oct-3-yl)-N'-(2-tert-butyloxyphenyl)urea (E25)

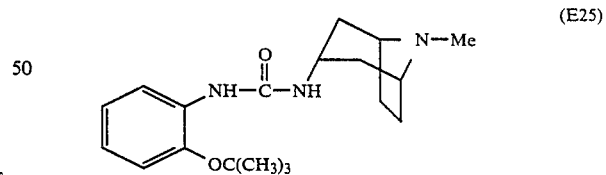

(E25)

m.p. 150°–1°.

| $^1$H—NMR (CDCl$_3$, 270 MHz) | |
|---|---|
| δ | 7.80 (dd, 1H) |
| | 7.07–6.86 (m, 4H) |
| | 5.38 (brd, 1H) |
| | 3.93 (m, 1H) |
| | 3.16 (brs, 2H) |
| | 2.31–2.17 (m, 5H including 2.29, s, 3H) |
| | 2.10–2.01 (m, 2H) |
| | 1.80–1.67 (m, 4H) |
| | 1.39 (s, 9H) |

(endo)-N-(8-Methyl-8-azabicyclo[3.2.1]oct-3-yl)-N'-(2-allyloxyphenyl)urea (E26)

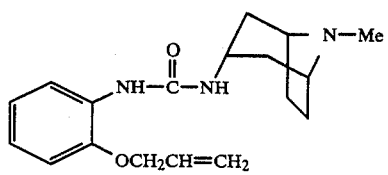
(E26)

m.p. 156°-7°.

| ¹H—NMR (CDCl₃, 270 MHz) | |
|---|---|
| δ | 7.89 (dd, 1H) |
| | 7.00–6.82 (m, 3H) |
| | 6.78 (s, 1H) |
| | 6.12–5.97 (m, 1H) |
| | 5.42–5.26 (m, 2H) |
| | 5.20 (brd, 1H) |
| | 4.58 (m, 2H) |
| | 3.96 (m, 1H) |
| | 3.16 (brs, 2H) |
| | 2.32–2.17 (m, 5H including 2.30, s, 3H) |
| | 2.12–2.03 (m, 2H) |
| | 1.78–1.66 (m, 4H) |

(endo)-N-(8-Methyl-8-azabicyclo[3.2.1]oct-3-yl)-N'-(2-phenoxyphenyl)urea (E27)

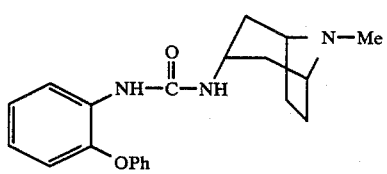
(E27)

m.p. 198°-9°.

| ¹H—NMR (CDCl₃, 270 MHz) | |
|---|---|
| δ | 8.06 (dd, 1H) |
| | 7.36–7.26 (m, 2H) |
| | 7.15–7.05 (m, 2H) |
| | 6.99–6.82 (m, 5H) |
| | 5.22 (brd, 1H) |
| | 3.90 (m, 1H) |
| | 3.11 (brs, 2H) |
| | 2.27 (s, 3H) |
| | 2.25–2.13 (m, 2H) |
| | 2.07–1.99 (m, 2H) |
| | 1.74–1.56 (m, 4H) |

EXAMPLE 28

(endo)-N-(8-Methyl-8-azabicyclo[3.2.1]oct-3-yl)-N'-(5-hydroxycarbonyl-2-methoxyphenyl)urea (E28)

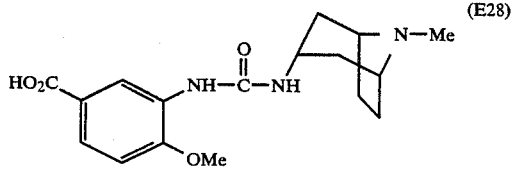
(E28)

The methyl ester (Example 19, 1.0 g) was heated under reflux in a methanol (10 ml) and aqueous (10 ml) solution of 2.5N NaOH (5 ml) for four hours. The methanol was removed in vacuo and the aqueous residue acidified to pH 7.0. The crystalline product was collected and dried (0.86 g).
m.p. 232°-5°.

| ¹H NM (CD₃OD/DCl, 270 MHz) | |
|---|---|
| δ | 8.70 (d, 1H) |
| | 7.67 (dd, 1H) |
| | 7.03 (d, 1H) |
| | 4.02–3.85 (m, 6H including 3.96, s, 3H) |
| | 2.80 (s, 3H) |
| | 2.56–2.35 (m, 6H) |
| | 2.17 (brd, 2H) |

EXAMPLE 29

(endo)-N-(8-Methyl-8-azabicyclo[3.2.1]oct-3-yl)-N'-(4-hydroxycarbonyl-2-methoxyphenyl)urea (E29)

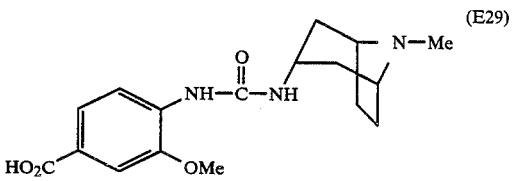
(E29)

Following the procedure outlined in Example 28, Example 11 was converted to the title compound.
m.p. 213°-20°.

| ¹H—NMR (CD₃OD/DCl, 270 MHz) | |
|---|---|
| δ | 8.14 (d, 1H) |
| | 7.57 (dd, 1H) |
| | 7.53 (d, 1H) |
| | 4.00–3.85 (m, 6H including 3.93, s, 3H) |
| | 2.80 (s, 3H) |
| | 2.60–2.30 (m, 6H) |
| | 2.16 (brd, 2H) |

EXAMPLE 30

(endo)-N-(8-Methyl-8-azabicyclo[3.2.1]oct-3-yl)-N'-(5-methylaminocarbonyl-2-methoxyphenyl)urea (E30)

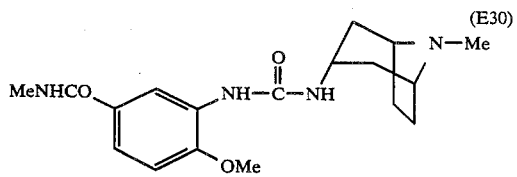
(E30)

A solution of Example 28 (0.5 g) in thionyl chloride (2 ml) was stirred at room temperature for 1 h. the thionyl chloride was removed in vacuo and the residue treated with a solution of methylamine (4 equivalents) in CH₂Cl₂ (25 ml). The reaction was stirred overnight, washed with aqueous NaHCO₃ solution, dried and concentrated. The residue was crystallised from ethyl acetate to give the title compound.

| ¹H NMR (d⁶-DMSO, 270 MHz) | |
|---|---|
| δ | 8.55 (d, 1H) |
| | 8.23–8.10 (m, 2H) |
| | 7.37 (dd, 2H) |

-continued

| $^1$H NMR (d$^6$-DMSO, 270 MHz) |
|---|
| 7.00 (d, 1H) |
| 6.91 (brd, 1H) |
| 3.90 (s, 3H) |
| 3.77 (q, 1H) |
| 3.23 (brs, 2H) |
| 2.73 (d, 3H) |
| 2.31 (s, 3H) |
| 2.20–1.90 (m, 6H) |
| 1.65 (brd, 2H) |

EXAMPLE 31

(endo)-N-(8-Methyl-8-azabicyclo[3.2.1]oct-3-yl)-N'-(5-hydroxy-2-methoxyphenyl)urea monohydrochloride (E31)

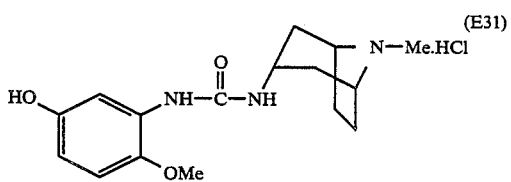

The 5-benzyloxy-2-methoxyphenyl isocyanate and (endo)-8-methyl-8-azabicyclo[3.2.1]octan-3-amine were converted via the procedure outlined in Example 1 to (endo)-N-(8-methyl-8-azabicyclo[3.2.1]oct-3-yl)-N'-(5-benzyloxy-2-methoxyphenyl)urea which was converted to the monohydrochloride salt.

The hydrochloride salt was hydrogenated at atmospheric pressure and room temperature over 10% Pd/C in ethanol to give the title compound.

| $^1$H NMR (d$_6$-DMSO, 270 MHz) | |
|---|---|
| δ | 8.81 (s, 1H) |
| | 8.10 (s, 1H) |
| | 7.68 (d, 1H) |
| | 7.16 (d, 1H) |
| | 6.75 (d, 1H) |
| | 6.24 (dd, 1H) |
| | 4.20–4.05 (m, 1H) |
| | 3.85–3.70 (m, 5H) |
| | 3.17 (d, 3H) |
| | 2.65 (s, 2H) |
| | 2.55–2.15 (m, 4H) |
| | 1.90 (brd, 2H) |

EXAMPLE 32

(Endo)-N-(8-Methyl-8-azabicyclo[3.2.1]oct-3-yl)-N'-(2-methoxycarbonylphenyl)urea (E32)

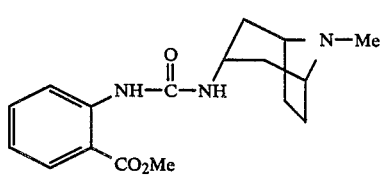

A solution of phosgene in toluene (12.5%, 7.5 ml) was added to a stirred solution of methyl anthranilate (1.2 g) in dry CH$_2$Cl$_2$ (100 ml) at 0° C. After 10 min, triethylamine (2.5 ml) was added. After a further 10 min, a solution of (endo)-8-methyl-8-azabicyclo[3.2.1]octan-3-amine (1.12 g) in CH$_2$Cl$_2$ (10 ml) was added and the reaction stirred to room temperature for 4 h. The reaction mixture was then washed with excess sat. NaHCO$_3$ solution, dried (K$_2$CO$_3$) and concentrated in vacuo. Recrystallisation of the residue from ethyl acetate/petrol gave the title compound (E32) (1.8 g) m.p. 125°–7°.

| $^1$H NMR (δ, CDCl$_3$) |
|---|
| 10.28 (brs, 1H) |
| 8.50 (dm, 1H) |
| 7.96 (dm, 1H) |
| 7.48 (tm, 1H) |
| 6.95 (tm, 1H) |
| 5.01 (ord, 1H) |
| 4.00 (q, 1H) |
| 3.90 (s, 3H) |
| 3.17 (brs, 2H) |
| 2.40–2.05 (m, 7H including 2.30, s, 3H) |
| 1.95–1.70 (m, 4H) |

EXAMPLES 33 TO 38

The following examples were prepared by a similar procedure to that described in Example 32.

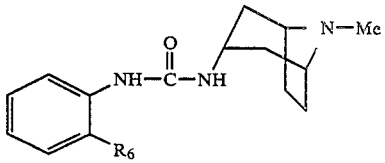

| Compound | R$_6$ | m.p. °C. |
|---|---|---|
| 33 | CO$_2$Et | 145–7 |
| 34 | CONMe$_2$ | 196–7 |
| 35 | SO$_2$NMe$_2$ | 162–3 |
| 36 | NO$_2$ | 177–8 |
| 37 | CH$_2$OCH$_3$ | 148–9 |
| 38 | SMe | 284–5* |

*hydrochloride salt.

Pharmacology

Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response (ED$_{50}$) was then determined.

The compound of Example 2 gave an ED$_{50}$ value of 2 μg/kg i.v.

The compounds of Examples 14, 15, 24, 26, and 27 were active at doses of 2, 3.4, 2.2, 22.5 and 1.8 μ/kg i.v. respectively.

I claim:

1. A compound of formula (I), or a pharmaceutically acceptable salt thereof:

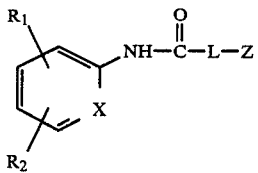

(I)

wherein

L is NH;

X is $N^+—O^-$, $COR_5$ wherein $R_5$ is hydrogen, $C_{1-6}$ alkyl, $C_{3-7}$ alkenyl-methyl, phenyl or phenyl $C_{1-4}$ alkyl in which either phenyl moiety may be substituted by one or two $C_{1-6}$ alkyl, $C_{1-6}$ alkoxy or halo, or $C—R_6$ wherein $R_6$ is $CO_2R_7$ wherein $R_7$ is hydrogen or $C_{1-6}$ alkyl, $CONR_8R_9$ or $SO_2NR_8R_9$ wherein $R_8$ and $R_9$ are independently hydrogen or $C_{1-6}$ alkyl or together are $C_{4-6}$ polymethylene, or $R_6$ is $NO_2$, $(CH_2)_mOR_{10}$ wherein m is 1 or 2 and $R_{10}$ is $C_{1-6}$ alkyl or $S(O)_nR_{11}$ wherein n is 0, 1 or 2 and $R_{11}$ is $C_{1-6}$ alkyl;

$R_1$ and $R_2$ are independently selected from hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, carboxy, $C_{1-6}$ alkoxycarbonyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene; and Z is a group of formula (a), (b) or (c)

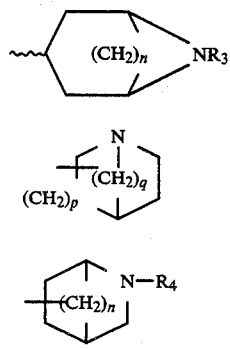

(a)

(b)

(c)

wherein n is 2 or 3; p is 1 or 2; q is 1 to 3; r is 1 to 3; and $R_3$ or $R_4$ is $C_{1-7}$ alkyl, $C_{3-8}$ cycloalkyl, $C_{3-8}$ cycloalkyl-$C_{1-2}$ alkyl or $C_{2-7}$ alkenyl-$C_{1-4}$ alkyl.

2. A compound according to claim 1 of formula (II):

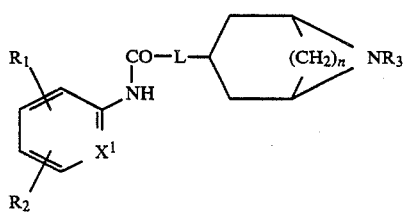

(II)

wherein $X^1$ is $COR_5$ or a group $C—R_6$ as defined in claim 1; and the remaining variables are as defined in claim 1.

3. A compound according to claim 2 wherein n is 2.

4. A compound according to claim 2 wherein $R_3$ is methyl or ethyl.

5. A compound according to claim 1 of formula (IV):

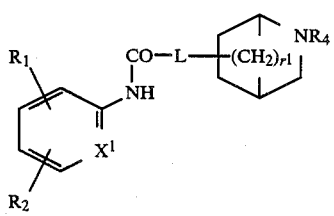

(IV)

wherein $r^1$ is 1 or 2 and $X^1$ is $COR_5$ or a group $C—R_6$.

6. A compound according to claim 5 wherein r' is 2.

7. A compound according to claim 1 wherein $R_1$ and $R_2$ are both hydrogen.

8. A compound according to claim 1 wherein X is $C—OCH_3$, $C—OC_2H_5$, $C—OC_3H_7$, $C—CO_2CH_3$, $C—CO_2C_2H_5$ or $C—SO_2N(CH_3)_2$.

9. A pharmaceutical composition for use in the treatment of migraine, cluster headache, trigeminal neuralgia and/or emesis, comprising an effective amount of a compound according to claim 1, and a pharmaceutically acceptable carrier.

10. A method of treatment of migraine, cluster headache, trigeminal neuralgia and/or emesis, in mammals, comprising the administration to the mammal in need of such treatment, an effective amount of a compound according to claim 1.

11. A compound selected from the group consisting of (endo)-N-(9-methyl-9-azabicyclo[3.3.1]non-3-yl)-N'-2-methoxyphenyl urea, (endo)-N-(8-methyl-8-azabicyclo[3.2.1]oct-3-yl)-N'-2-methoxyphenyl urea, (endo)-N-(8-methyl-8-azabicyclo[3.2.1]oct-3-yl)-N'-(2-pyridyl-1-oxide)urea, (endo)-N-(8-methyl-8-azabicyclo[3.2.1]oct-3-yl)-N'-(5-fluoro-2-methoxyphenyl)urea, (endo)-N-(8-methyl-8-azabicyclo[3.2.1]oct-3-yl)-N'-(2,4-dimethoxyphenyl)urea, (endo)-N-(8-methyl-8-azabicyclo[3.2.1]oct-3-yl)-N'-(2-methoxy-5-methylphenyl)urea, (endo)-N-(8-methyl-8-azabicyclo[3.2.1]oct-3-yl)-N'-(5-chloro-2-methoxyphenyl)urea, (endo)-N-(8-methyl-8-azabicyclo[3.2.1]oct-3-yl)-N'-(2,5-dimethoxyphenyl)urea, (endo)-N-(8-methyl-8-azabicyclo[3.2.1]oct-3-yl)-N'-(2-methoxy-5-nitrophenyl)urea, (endo)-N-(8-methyl-8-azabicyclo[3.2.1]oct-3-yl)-N'-(2-methoxy-4-methoxycarbonylphenyl)urea, (endo)-N-(8-methyl-8-azabicyclo[3.2.1]oct-3-yl)-N'-(2-ethoxy-5-fluorophenyl)urea, (endo)-N-(8-methyl-8-azabicyclo[3.2.1]oct-3-yl)-N'-(4-fluoro-2-methoxyphenyl)urea, N-(1-azabicyclo[2.2.2]oct-3-yl)-N'-(2-methoxyphenyl)urea, (endo)-N-(8-methyl-8-azabicyclo[3.2.1]oct-3-yl)-N'-(2-n-propyloxyphenyl)urea, (endo)-N-(8-methyl-8-azabicyclo[3.2.1]oct-3-yl)-N'-(2-ethoxyphenyl)urea, (endo)-N-(8-methyl-8-azabicyclo[3.2.1]oct-3-yl)-N'-(5-dimethylaminocarbonyl-2-methoxyphenyl)urea,
(endo)-N-(8-methyl-8-azabicyclo[3.2.1]oct-3-yl)-N'-(5-methoxycarbonyl-2-methoxyphenyl)urea,
(endo)-N-(8-methyl-8-azabicyclo[3.2.1]oct-3-yl)-N'-(2-iso-propoxyphenyl)urea,
(endo)-N-(8-methyl-8-azabicyclo[3.2.1]oct-3-yl)-N'-(2-benzyloxyphenyl)urea,
(endo)-N-(8-methyl-8-azabicyclo[3.2.1]oct-3-yl)-N'-(2-hydroxyphenyl)urea,
(endo)-N-(8-methyl-8-azabicyclo[3.2.1]oct-3-yl)-N'-(2-sec-butyloxyphenyl)urea,
(endo)-N-(8-methyl-8-azabicyclo[3.2.1]oct-3-yl)-N'-(2-n-butyloxyphenyl)urea,
(endo)-N-(8-methyl-8-azabicyclo[3.2.1]oct-3-yl)-N'-(2-tert-butyloxyphenyl)urea,
(endo)-N-(8-methyl-8-azabicyclo[3.2.1]oct-3-yl)-N'-(2-allyloxyphenyl)urea,
(endo)-N-(8-methyl-8-azabicyclo[3.2.1]oct-3-yl)-N'-(2-phenoxyphenyl)urea,
(endo)-N-(8-methyl-8-azabicyclo[3.2.1]oct-3-yl)-N'-(5-hydroxycarbonyl-2-methoxyphenyl)urea,
(endo)-N-(8-methyl-8-azabicyclo[3.2.1]oct-3-yl)-N'-(4-hydroxycarbonyl-2-methoxyphenyl)urea,
(endo)-N-(8-methyl-8-azabicyclo[3.2.1]oct-3-yl)-N'-(5-methylaminocarbonyl-2-methoxyphenyl)urea,
(endo)-N-(8-methyl-8-azabicyclo[3.2.1]oct-3-yl)-N'-(5-hydroxy-2-methoxyphenyl)urea,
(endo)-N-(8-methyl-8-azabicyclo[3.2.1]oct-3-yl)-N'-(2-methoxycarbonylphenyl)urea,
(endo)-N-(8-methyl-8-azabicyclo[3.2.1]oct-3-yl)-N'-(2-ethoxycarbonylphenyl)urea,
(endo)-N-(8-methyl-8-azabicyclo[3.2.1]oct-3-yl)-N'-(2-dimethylaminocarbonylphenyl)urea,
(endo)-N-(8-methyl-8-azabicyclo[3.2.1]oct-3-yl)-N'-(2-dimethylaminosulphonylphenyl)urea,
(endo)-N-(8-methyl-8-azabicyclo[3.2.1]oct-3-yl)-N'-(2-nitrophenyl)urea,
(endo)-N-(8-methyl-8-azabicyclo[3.2.1]oct-3-yl)-N'-(2-methoxymethylphenyl)urea,
(endo)-N-(8-methyl-8-azabicyclo[3.2.1]oct-3-yl)-N'-(2-methylthiophenyl)urea, or pharmaceutically acceptable salts of any of the foregoing.

12. (endo)-N-(8-Methyl-8-azabicyclo[3.2.1]oct-3-yl)-N'-(2-phenoxyphenyl)urea or a pharmaceutically acceptable salt thereof.

* * * * *

UNITED STATES PATENT AND TRADEMARK OFFICE
CERTIFICATE OF CORRECTION

PATENT NO. : 4,797,387
DATED : January 10, 1989
INVENTOR(S) : Francis D. King

It is certified that error appears in the above-identified patent and that said Letters Patent is hereby corrected as shown below:

Title page:

Abstract, formula (c), "n" should be -- r --;

Column 1, formula (c), "n" should be -- r --;

Claim 1, formula (c), "n" should be -- r --;

Claim 6, "r'" should be -- $r^1$ --.

Signed and Sealed this

Sixth Day of November, 1990

Attest:

HARRY F. MANBECK, JR.

*Attesting Officer*  *Commissioner of Patents and Trademarks*